United States Patent [19]

Glushkov et al.

[11] 4,088,647
[45] May 9, 1978

[54] PYRAZINO (1,2,3-ab)-β-CARBOLINE DERIVATIVES AND SALTS THEREOF AND METHOD OF PREPARING SAME

[76] Inventors: Robert Georgievich Glushkov, ulitsa Gorkogo, 43, kv. 90; Mikhail Davydovich Mashkovsky, Leningradsky prospekt, 75a, kv. 55; Natalia Ivanovna Andreeva, Frunzenskaya naberezhnaya, 54, kv. 8; Serafima Solomonovna Liberman, ulitsa Arbat, 51, kv. 78; Leonid Nikonovich Gerchikov, Kooperativnaya ulitsa, 2, korpus 13, kv. 54; Vera Alexeevna Volskova, ulitsa Matveevskaya, 10, korpus 4, kv. 286; Antonida Vasilievna Zaitseva, Belovezhskaya ulitsa, 17, kv. 24, all of Moscow, U.S.S.R.; Onisim Julievich Magidson, deceased, late of Moscow, U.S.S.R., by Galina Konstantinovna Magidson; by July Onisimovich Magidson, administrators, both of Mytnaya ulitsa, 28, kv. 46, Moscow, U.S.S.R.

[21] Appl. No.: 746,688

[22] Filed: Dec. 2, 1976

Related U.S. Application Data

[63] Continuation of Ser. No. 655,020, Feb. 4, 1976, abandoned, which is a continuation of Ser. No. 415,841, Nov. 14, 1973, abandoned.

[51] Int. Cl.² .......................................... C07D 471/14
[52] U.S. Cl. .............................. 544/343; 260/243.3; 260/296 P; 260/326.5 B; 260/326.9; 424/250
[58] Field of Search ................................ 260/268 PC

*Primary Examiner*—Jose Tovar
*Attorney, Agent, or Firm*—Holman & Stern

[57] ABSTRACT

New tetracyclic compounds, containing indole nucleus in their structure, having the general formula

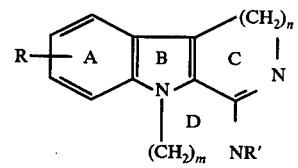

where R is hydrogen, alkyl, or alkoxyl, R' is an alkyl, and $m$ and $n$ are 2 or 3.

The said compounds react with organic and mineral acids to form salts readily soluble in water.

The method for preparing the said compounds consists in cyclization of lactams, having the general formula

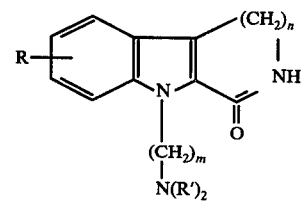

where R, R', $m$ and $n$ are as specified above, or of their hydrochlorides by phosphorus oxychloride.

2 Claims, No Drawings

PYRAZINO (1,2,3-ab)-β-CARBOLINE DERIVATIVES AND SALTS THEREOF AND METHOD OF PREPARING SAME

This is a continuation of application Ser. No. 655,020, filed Feb. 4, 1976, now abandoned, which in turn is a continuation of application Ser. No. 415,841, filed Nov. 14, 1973, now abandoned.

This invention relates to condensed derivatives of indole, and more particularly to new tetracyclic compounds containing an indole nucleus in its structure, the salts thereof, and the method of preparing both.

Condensed indole derivatives are known in the prior art which include, tetracyclic compounds containing an indole nucleus, among which are both synthetic and natural substances possessing high physiological potency (derivatives of lysergic acid, reserpin, etc). In this connection, the said substances are of great practical importance.

The object of this invention is to synthesize a new group of tetracyclic compounds containing an indole nucleus which seem to offer good prospects in developing new efficaceous medicinal preparations.

Proposed herein are new tetracyclic compounds containing an indole nucleus in their structure namely, pyrazino (1,2,3-ab)-β-carboline derivatives which according to the invention, have the general formula (1)

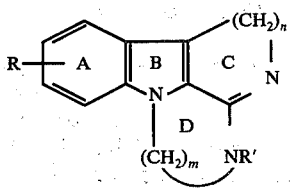

where R is hydrogen, alkyl, or alkoxyl, R' is an alkyl, and m and n are 2 or 3.

The compounds having the formula (1) are essentially solid substances having basic properties, which are readily soluble in most organic solvents, dilute acids, and sparingly soluble in water. These compounds react with organic or mineral acids to form salts which are readily soluble in water, and which can be described by the following formula

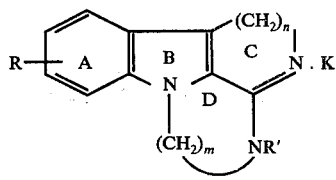

where R, R', m and n are as specified above, while K is an organic or a mineral acid.

Among the above named compounds, substances were developed that possess high psychotropic potency, for example, the compound 3-methyl-8-methoxy-3H,1,2,5,6-tetrahydropyrazine-[1,2,3-ab]-β-carbolin hydrochloride, can be used to treat depressive states and other mental disorders.

The experimental data show that this compound produces a marked effect on the central and autonomous nervous systems. It intensifies the central effects of phenamine and 5-hydroxytriptophane and the peripheral action of adrenaline, phenylethylamine tyramine, serotonine and triptamine. The compound lessens the damping effect of reserpine and tetrabenzine, and also the cataleptic activity of phenothiazine derivatives. These pharmacological properties characterize the preparation as one similar to antidepressive substances.

Unlike all other antidepressants, the new preparation does not produce cholinolytic action, but promotes the hypnotic effect of hexanal, the analgetic action of promedole, the local anesthetic action of novocaine, and stronger than imizine in that it intensifies the effect of phenylethylamine, tyramine and triptamine. According to the data of biochemical studies of the preparation, when given in doses sufficient to produce pronounced therapeutic effect, it moderately inhibits the monoaminoxydase activity only in kidney tissues, which makes it possible to suggest that the antimonoaminoxydase action does not underlie the pharmacological effect of this compound. The toxicological studies of the preparation on mice, rats and rabbits, with single and multiple administrations, have shown that when given in doses 30–50 times exceeding that of the recommended, it does not produce a toxic action on the animals. The clinical trials of the compound have proved its antidepressive potency which is associated with the stimulating effect. According to the data of the clinical tests, this preparation is indicated for treatment of apathic, adynamic, neurotic and slight hypochondriac depressive conditions. Owing to insignificant side effects, this preparation can be recommended for treating patients under both stationary and out-patient conditions.

The proposed compound can also be used for the treatment of psychic diseases in combination with neuroleptics. It can be given in the form of tablets, powder, or injection solutions.

According to the invention, the method of preparing the compounds having the general formula (1) consists in the cyclization of lactams having the general formula (2)

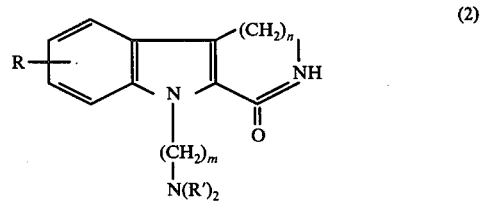

where R, R', n and m are as specified for formula (1), or of their hydrochlorides, by phosphorus oxychloride, with the formation of intermediate compounds having the general formula (3)

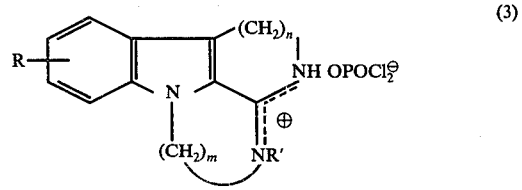

where R, R', m and n are the same as in formula (2), and with their subsequent transformation into the final product.

The intermediate compound having the formula (3) can be converted into the final product by the following two methods:
(a) either by processing the compounds having the formula (3) by an alkaline agent, or (b) by processing the intermediate product having the formula (3) by a lower aliphatic alcohol.

The proposed method can be realized as follows:

(a) Lactams having the general formula (2) undergo cyclization by phosphorus oxychloride, preferably with heating, to give the intermediate compound having the formula (3). The excess phosphorus oxychloride is removed by distillation, while the residue is treated in the cold by an aqueous solution of an alkaline agent. The prepared product having the formula (1) is extracted by an organic solvent, preferably with benzene or chloroform. Whenever required, the product having the formula (1) can be converted into the corresponding salt by the action of an organic or a mineral acid.

(b) Lactams having the general formula (2) undergo cyclization by phosphorus oxychloride at elevated temperatures. The thus formed intermediate product having the formula (3) is separated and processed, preferably by heating, with a lower aliphatic alcohol, for example, ethyl alcohol, with subsequent isolation of the final product after cooling.

The starting compounds, according to the present invention, are lactams having the general formula (2), of which some are known substances, while others are novel compounds. These starting compounds can be prepared from derivatives of β-carboline and azepino-[3,4-b]indole by the known methods.

For a better understanding of the invention, the following examples of its practical embodiment will hereinafter be given by way of illustration.

Example 1 illustrates the preparation of the starting lactams and their hydrochlorides according to formula (2).

EXAMPLE 1

(a) The preparation of 1-oxo-10(β-dimethylaminoethyl)-1H,2,3,4,5-tetrahydroazepine-[3,4-b]-indole having the formula (2), where $m$ is 2, $n$ is 3, R=H; R' is $CH_3$.

A suspension of 20 g of 1-oxo-1H-2,3,4,5-tetrahydroazepine[3,4-b]-indole in 120 ml of dry dimethylformamide at a temperature of 25° C combined with are 3 g of sodium hydride added in portions. The mixture is heated for 2 hours at 30° C and for 30 minutes at 50° C. Then 14 g of β-dimethylaminoethyl chloride is added dropwise to the reaction mixture, whereupon the mixture is heated for 4 hours at 50°-55° C and then allowed to stand overnight. Then 100 ml of a 50 percent solution of acetic acid are added, and the mixture is passed through a filter, made alkaline by a 15 percent solution of aqueous ammonia to pH of about 9 and extracted with benzene. The extract is washed with water, dried by calcined potash, evaporated, whereupon the residue is triturated with ether, and dried to give 14.2 g of the compound having the formula (2). The yield is 52.4 percent, and the melting point is 122°-123° C (ethylacetate).

Found, in percent: C, 70.83; H, 7.50, 15.56. $C_{10}H_{21}N_3O$. Calculated, in percent: C, 70.84; H, 7.75; 15.50.

The hydrochloride: m.p. 253°-254° C (alcohol).

Found, in percent: N, 14.00; Cl, 11.28. $C_{16}H_{27}N_3O.HCl$. Calculated, in percent: N, 13.65; Cl, 11.55.

Other lactams having the formula (2), and their hydrochlorides, are prepared by similar synthesis.

(b) 1-Hydroxo-10 (γ-dimethylaminopropyl)-1H,2,3,4,5-tetrahydrozepine[3,4-b]indole hydrochloride, where $m=n=3$, R=H, and R'=$CH_3$; m.p. 170°-171.5° C.

Found, in percent: C, 63.54; H, 7.33; N, 13.00; Cl, 10.76. $C_{17}H_{23}N_3O.HCl$. Calculated, in percent: C, 63.45; H, 7.46; N, 13.00; Cl, 11.04.

(c) 1-Hydroxo-10-(β-diethylaminoethyl)-1H,2,3,4,5-tetrahydroazepine [3,4-b]-indole having the formulas (2) where $m = 2$, $n = 3$, R = H, R' = $C_2H_5$. The yield is 36.7 percent of theory, m.p. 112°-113° C (petroleum ether).

Found in percent: C, 72.38; H, 8.30; N, 14.01. $C_{18}H_{25}N_3O$. Calculated, in percent: C, 72.24; H, 8.25; N, 14.04.

The hydrochloride: m.p. 232°-234° C (ethylacetate). Found, in percent: C, 64.54; H, 8.08; Cl, 10.52; N, 12.83. $C_{18}H_{25}N_3O.HCl$ Calculated, in percent: C, 64.35; H, 7.47; Cl, 10.58; N, 12.51.

(d) 1-hydroxo-9-(β-dimethylaminoethyl)-1,2,3,4-tetrahydro-β-carboline having the formula (2) where $m = 2$, $n = 2$, R=H, R'=$CH_3$. The yield is 65 percent of theory; m.p. 123°-124° C.

Found in percent: C, 70.10; H, 7.16; N, 15.87. $C_{15}H_{19}N_3O$. Calculated, in percent: C, 70.03; H, 7.39; N, 16.30.

The hydrochloride, m.p. 231°-232° C

Found, in percent: C, 12.14; N, 14.34. $C_{15}H_{19}N_3O.HCl$ Calculated, in percent: C, 12.08; N, 14.31.

(e) 1-hydroxo-7-methoxy-9-(β-dimethylaminoethyl)-1,2,3,4-tetrahydro-β-carboline having the formula (2) where $m = 2$, $n = 2$, R = 7-methoxy, R' = $CH_3$.

Found, in percent: C, 67.10; H, 7.51; N, 14.75. $C_{16}H_{21}N_3O_2$. Calculated, in percent: C, 66.89; H, 7.31; N, 14.63.

The hydrochloride: m.p. 279°-280° C.

Found, in percent: C, 10.75; N, 13.65. $C_{16}H_{21}N_3O_2.HCl$. Calculated, in percent: C, 10.97; N, 13.00.

EXAMPLE 2

Preparation of the compound having the formula (1) where $m = 2$, $n = 3$, R = H, and R' = $CH_3$.

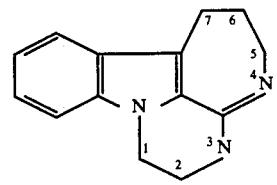

A mixture of 2 g of the lactam prepared in Example 1.a, and 10 ml of phosphorus oxychloride is heated for 4 hours, evaporated to dryness in vacuum, the residue (which is an intermediate product having the formula (3), where $m = 2$, $n = 3$, R = H and R' = $CH_3$) is cooled, processed by an aqueous solution of ammonia, extracted with benzene, dried by potash, and then evaporated. The yield of the product is about 50 percent of theory; the m.p. 138°-139° C (hexane).

Found, in percent: C 75.50; H 7.00; N 17.70. $C_{15}H_{17}N_3$. Calculated, in percent: C 75.31; H 7.11; N 17.57.

The bitartrate: m.p. 216°-218° C.

EXAMPLE 3

Preparation of 23-methyl-8-methoxy-2H,1,2,3,5,6-tetrahydropyrosine-[1,2,3-ab]-β-carboline having the formula (1) where m and n are 2, R is 8-methoxy and R' is CH₃

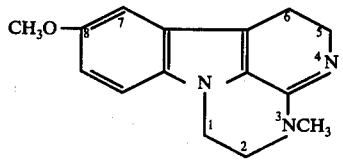

A mixture of 2 g of 1-hydroxo-6-methoxy-9-[-β-dimethylaminoethyl]-1,2,3,4-tetrahydro-β-carboline hydrochloride and 10 ml of phosphorus oxychloride is heated for 4 hours and evaporated in vacuum to dryness. The residue, which is a product having the formula (3), where $m=n=2$, R is 8-methoxy, and R'=CH₃ is cooled and processed by an aqueous solution of ammonia. The solution is extracted with chloroform, and extract is dried by calcined sodium sulphate and evaporation.

The yield of the product is 1.1 g, which is 70 percent of theory; the melting point, 164° - 166° C (water-CH₃OH).

Found, in percent: C, 70.40; H, 6.73; N, 16.50. $C_{15}H_{17}N_3O$. Calculated, in percent: C, 70.58; H, 6.66; N, 16.47.

The semihydrate of the bitartrate: m.p. ≈ 220° C (dimethylformamide).

Found, in percent: C, 60.42; H, 6.03; N, 12.50; H₂O 2.48. $C_{15}H_{17}N_3O \cdot 0.5H_6C_4 \cdot 0.5H_2O$. Calculated, in percent: C, 60.18; H, 6.19; N, 12.39; and H₂O 2.65.

EXAMPLE 4

Preparation of the compound having the formula (1) where $m = 3$, $n = 3$, R = H and R' = CH₃.

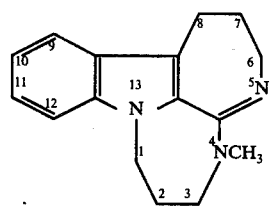

The procedure is similar to that described in Example 3 except that the starting substance is a lactam having the formula (2) where m and n are 3, R is H, and R' is CH₃. The melting point of the product is 168°-170° C.

Found, in percent: C, 76.04; H, 7.65; N, 16.52; $C_{16}H_{19}N_3$. Calculated, in percent: C, 75.89; H, 7.51; N, 16.60.

EXAMPLE 5

Preparation of the compound having the formula (1) where m is 2, n is 3, R is H and R' is C₂H₅

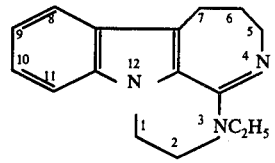

The procedure is the same as in Example 3, except that the starting substance is the hydrochloride of a lactam having the formula (2), where m is 2, n is 3, R is H and R' is C₂H₅.

The yield of the product is 40 percent of theory; the melting point is 131°-132° C.

Found, in percent: C, 76.12; H, 7.73; N, 16.86. $C_{16}H_{19}N_3$.

Calculated, in percent: C, 75.88; H, 7.51; N, 16.60.

EXAMPLE 6

Preparation of the compound having the formula (1) where m and n are 2, R is H and R' is CH₃

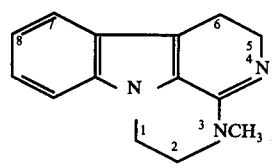

The procedure is the same as in Example 3, except that the starting substance is the hydrochloride of lactam having the formula (2) where m and n are 2, R is H and R' is CH₃.

The yield of the product is 70 percent of theory. The melting point is 102°-103° C.

Found, in percent: C, 74.90; H, 6.53; N, 18.70. $C_{14}H_{15}N_3$ Calculated, in percent: C, 74.66; H, 6.86: N, 18.66.

The hydrochloride: m.p. below 350° C.

Found, in percent: Cl, 13.5; N, 15.65. $C_{14}H_{15}N_3 \cdot HCl$ Calculated, in percent: Cl, 13.57; N, 16.06.

EXAMPLE 7

Preparation of the compound having the formula (1) where m and n are 2, R is 9-methoxy, and R' is CH₃

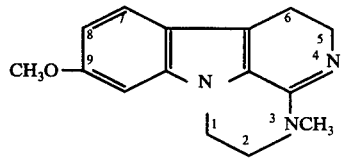

The procedure is the same as in Example 3, except that the starting substance is the hydrochloride of a lactam having the formula (2) where m and n are 2, R is 9-methoxy and R' is CH₃. The yield of the product is 80 percent of theory; the m.p. 108°-109° C.

Found, in percent: C, 70.20; H, 6.80; N, 16.85. $C_{15}H_{17}N_3O$. Calculated, in percent: C, 70.58; H, 6.66; N, 16.47.

The hydrochloride: m.p. 275° C.

Found, in percent: Cl, 12.24; N, 14.65; $C_{15}H_{17}N_3O \cdot HCl$. Calculated, in percent: Cl, 12.17; N, 14.40.

EXAMPLE 8

Preparation of the compound having the formula (1) where m is 3, n is 2, R is 9-methoxy, and R' is CH₃

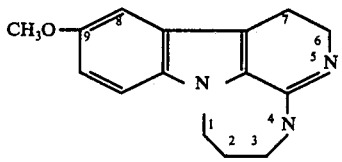

The process is similar to that described in Example 3, except that the starting substance is the hydrochloride of a lactam having the formula (2) where m is 3, n is 2, R is 9-methoxy, and R' is CH₃. The yield of the product is 71 percent of theory; the melting point, 140°–141° C.

Found, in percent: C, 75.77; H, 7.50; N, 16.91. Calculated in percent: C, 75.88; H, 7.51; N, 16.60.

EXAMPLE 9

Preparation of 3-methyl-8-methoxy-3H,1,2,5,6-tetrahydropyrazine-[1,2,3-ab]-β-carboline hydrochloride, where m and n are 2, R is 8-methoxy, and R' is CH₃.

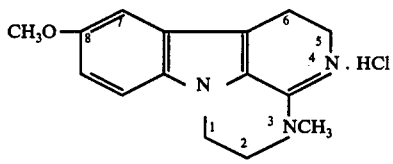

A mixture of 162 g of 9-[β(N,N-dimethylamine)ethyl-6-methoxy-1-hydroxo-1,2,3,4-tetrahydro-β]-carboline and 1 liter of phosphorus hydrochloride is boiled for 4 hours. As a result of heating, a precipitate falls out of the solution. The reaction mixture is cooled to 20° C, passed through a filter, whereupon the precipitate is washed with ether or benzene, and dried in order to prepare 3-methyl-3-methoxy-3H,1,2,5,6-tetrahydropyrazine-[1,2,3-ab]-β-carboline dichlorophosphonate. The yield is 132 g which is 93 percent of theory. The melting point is 196°–198° C.

Found, in percent: C, 46.48; H, 4.78; N, 10.94; P, 7.96. C₁₅H₁₈Cl₂N₃O₃P. Calculated, in percent: C, 46.15; H, 4.61; N, 10.76; P, 7.94.

The mixture of 182 g of 3-methyl-8-methoxy-3H,1,2,5,6-tetrahydropyrazine-(1,2,3-ab)-β-carboline dichlorophosphonate (3) and 1 liter of absolute ethylalcohol is boiled with stirring for 1 hour. In the process of heating, a solution is formed from which a precipitate falls out. The reaction mixture is cooled on ice (for 60–90 minutes), whereupon the precipitate is separated on a filter, washed with cold absolute ethyl alcohol, and dried to prepare 3-methyl-8-methoxy-3H,1,2,5,6-tetrahydropyrazine-(1,2,3-ab)-β-carboline hydrochloride, where m and n are 2, R is 8-methoxy, R' is CH₃. The yield is 130.5 g which is 95 percent of theory; the m.p. 306°–309° C.

Found, in percent: C, 61.65; H, 6.00; Cl, 12.11; N, 14.37. C₁₅H₁₇N₃O.HCl. Calculated, in percent: C, 61.75; H, 5.83; Cl, 12.17; N, 14.40.

We claim:
1. A compound of the formula

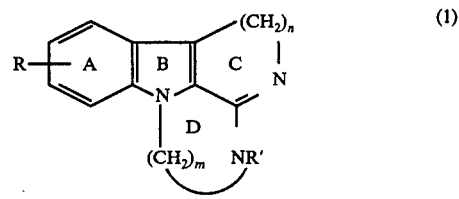

(1)

where R is selected from the group, consisting of hydrogen, methoxy or lower alkyl, R' is lower alkyl, m is 2 and n is 2.

2. 3-Methyl-8-methoxy-3H-1,2,5,6-tetrahydropyrazine-(1,2,3-ab)-β-carboline hydrochloride.

* * * * *